United States Patent
Eriksson et al.

(10) Patent No.: US 8,426,205 B2
(45) Date of Patent: Apr. 23, 2013

(54) METHOD FOR SELECTIVE ELECTROFUSION OF AT LEAST TWO FUSION PARTNERS HAVING CELL-LIKE MEMBRANES

(75) Inventors: Peter Eriksson, Göteborg (SE); Daniel T. Chiu, Seattle, WA (US); Alexander Moscho, München (DE); Owe Orwar, Hovås (SE); Richard N. Zare, Stanford, CA (US)

(73) Assignee: Collectricon AB, Gothenburg (SE)

( * ) Notice: Subject to any disclaimer, the term of this patent is extended or adjusted under 35 U.S.C. 154(b) by 0 days.

(21) Appl. No.: 13/555,946

(22) Filed: Jul. 23, 2012

(65) Prior Publication Data
US 2013/0052737 A1 Feb. 28, 2013

Related U.S. Application Data

(63) Continuation of application No. 10/031,410, filed as application No. PCT/SE00/01484 on Jul. 13, 2000, now abandoned.

(30) Foreign Application Priority Data

Jul. 30, 1999 (SE) .................................. 9902817-7

(51) Int. Cl.
*C12N 15/06* (2006.01)
(52) U.S. Cl.
USPC ......... 435/450; 435/173.9; 435/461; 424/450
(58) Field of Classification Search .................. None
See application file for complete search history.

(56) References Cited

U.S. PATENT DOCUMENTS

| | | | |
|---|---|---|---|
| 4,894,343 A | 1/1990 | Tanaka et al. |
| 4,970,154 A | 11/1990 | Chang |
| 4,994,384 A | 2/1991 | Prather et al. |
| 5,827,736 A | 10/1998 | Heller et al. |
| 6,010,613 A | 1/2000 | Walters et al. |
| 6,020,170 A | 2/2000 | Steenbakkers |
| 6,041,252 A | 3/2000 | Walker et al. |
| 6,093,557 A | 7/2000 | Pui et al. |

FOREIGN PATENT DOCUMENTS

| | | |
|---|---|---|
| JP | 8322568 A | 12/1996 |
| JP | 10180659 A | 7/1998 |
| WO | WO-98/56893 A1 | 12/1998 |

OTHER PUBLICATIONS

Office Action from JP Foreign Associate dated Apr. 27, 2011 for JP 2001-514089.
Chiu D.T. et al. "Chemical transformations in individual ultrasmall biomimetic containers.Science." Mar. 19, 1999;283(5409):1892-5.
Magae et al. "Electrofusion of giant protoplasts of *Pleurotus cornicoplae*." Appl. Micorbiol Biotechnol. 1986, 24:509-511.
Sakai RR et al. "Cloning and assisted reproductive techniques: influence on early development and adult phenotype" Birth Defects Res C Embryo Today. Jun; 75(2):151-62, (2005).
Mekid H. et al. in vivo cell electrofusion. Biochim Biophys Acta. Dec. 15; 1524(2-3):118-30, (2000).
Orentas RJ et al. "Electrofusion of a weakly immunogenic neuroblastoma with dendritic cells produces a tumor vaccine" Cell Immunol. Oct. 10;213(1):4-13, (2001).
Niemann H. et al. "Progress in reproductive biotechnology in swine." Theriogenology. Nov. 1, 2001; 56(8), Abstract, (2001).
Prasad G, et al. "Recent advances in experimental molecular therapeutics for malignant gliomas" Curr Med Chem Anticancer Agents. Jul. 2004;4(4):347-61.
Niculescu-Duvaz I, et al. Introduction to the background, principles, and state of the art in suicide gene therapy. Mol Biotechnol. May 2005;30(1):71-88.
Hans-Ulrich Koop et al., "regenration of Plants After Electrofusion of Selected Pairs of Protoplasts." European Journal of Cell Biology. vol. 39, pp. 46-49 (1985).
Stromberg et al., "Manipulating the Genetic Identity and Biochemical Surface Properties of Individual Cells With Electrical-Field-Induced Fusion." PNAS, vol. 97, No. 1. pp. 7-11 (2000).
Kranz et al. "In Vitro Fertilization of Single, Isolated Gametes of Maize Mediated by Electrofusion" Sex Plant Reprod. vol. 4, pp. 12-16 (1991).
Kranz et al., "Angiosperm Fertilisation, Embryo and Endosperm Development in Vitro" Plant Science, vol. 142, pp. 183-197, (1999).
Krantz et al., "Endosperm Development After Fusion of Isolated, Single Maize Sperm and Central Cells in Vitro," The Plant Cell, vol. 10, pp. 511-524 (1988).

*Primary Examiner* — Jim Ketter
(74) *Attorney, Agent, or Firm* — Edwards Wildman Palmer LLP; David G. Conlin; Lisa Swiszcz

(57) ABSTRACT

Disclosed is a method for selective electrofusion of at least two fusion partners having cell-like membranes and cellular or subcellular dimensions, comprising the following steps: A) the fusion partners are brought into contact with each other and B) an electrical field of a strength sufficient to obtain fusion and highly focused on the fusion partners is applied. The fusion partners are independently selected from the group consisting of a single cell, a liposome, a proteoliposome, a synthetic vesicle, an egg cell, an enucleated egg cell, a sperm cell at any development stage and a plant protoplast.

25 Claims, 5 Drawing Sheets

METHOD FOR SELECTIVE ELECTROFUSION OF AT LEAST TWO FUSION PARTNERS HAVING CELL-LIKE MEMBRANES

This application is a continuation of U.S. patent application Ser. No. 10/031,410, filed Jun. 21, 2002, which is a U.S. national phase application pursuant to 35 U.S.C. §371 of international application no. PCT/SE00/01484 filed Jul. 13, 2000, which designated the United States and was published in English on Feb. 8, 2001, under publication number WO 01/09297 A1, and which claims priority under 35 U.S.C. §119 to Swedish Application No 9902817-7 filed Jul. 30, 1999. The entire contents of each of the aforementioned applications is expressly incorporated herein by reference in their entireties.

FIELD OF THE INVENTION

The present invention relates to a method for selective electrofusion of at least two fusion partners having cell-like membranes.

BACKGROUND OF THE INVENTION

Electrofusion has developed into an extremely efficient method for the fusion of mammalian cells, mainly because of its mild conditions, which result in a high number of viable fusion products [see e.g. White, K. L. 1995, Electrofusion of mammalian cells, Methods in Molecular Biology, 48, 283-293]. The application of an electrical field over phospholipid bilayer membranes induces pore formation when the applied potential reaches or exceeds the membrane breakdown potential. Consequently, electro-permeabilization techniques has been used in a wide variety of biological experiments, like electrofusion for the creation of hybridomas and new cell lines [see e.g. Zimmermann, U., et al., 1985, Electrofusion: a novel hybridization technique, Adv. Biotechnol. Proc. 4, 79-150; Neil, G. A. et al., 1993. Electrofusion, Methods in Enzymology, 220, 174-196; Glassy, M. 1988, Product review: Creating hybridomas by electrofusion, Nature, 333, 579-580], in vitro fertilization [see e.g. Ogura, A. et al., 1995, Spermatids as male gametes. Reprod. Fertil. Dev., 7, 155-159], cloning experiments [see e.g. Van Stekelenburg-Hamers, A. E. P., et al., 1993, Nuclear transfer and electrofusion in bovine in vitro-matured/in vitro-fertilized embryos: effect of media and electrical fusion parameters, Mol. Reprod. Dev., 36, 307-312], electroporation of cells for introduction of cell-impermeant solutes [see e.g. Electroporation: a general phenomenon for manipulating cells and tissues, J. Cell. Biochem., 51: 426-435; Li, H., et al., 1997, Transfection of rat brain cells by electroporation, J. Neurosci. Methods, 75, 29-32; Lundqvist, J. A., et al., 1998, Altering the biochemical state of individual cultured cells and organelles with ultramicroelectrodes, Proc. Natl. Acad. Sci. USA, 95, 10356-10360], and electro-insertion for the addition of membrane-associated macromolecules, including proteins [see e.g. Mouneimne, Y., et al., 1989, Electro-insertion of xeno-glycophorin into the red blood cell membrane, Biochem. Biophys. Res. Com. 159, 34-40]. Applications of in vivo electrofusion include the incorporation of gonococcal attachment receptors from human HL60 cells to rabbit corneal epithelial tissue as a viable model of human-specific pathogens [see e.g. Heller, R., et al., 1990, Transfer of human membrane surface components by incorporating human cells into intact animal tissue by cell-tissue electrofusion in vivo, Biochim. Biophys. Acta, 1024, 185-188].

Electric-field-induced fusion is widely employed in biomedical research for a population of cells in suspension. Cells are first brought into contact by dielectrophoresis through the application of a low-amplitude, high-frequency AC field and subsequently a fraction of the cells are fused by a strong and short DC pulse. Bulk electrofusion of large quantities of cells is useful for creating and selecting new cell lines, but cannot be applied to fuse single cells with high precision. This leads to unwanted fusion between cells from the same cell-line, as well as the wanted fusion between cells from different cell lines. Furthermore, bulk electrofusions do not allow the control over the number of cells that are to be fused together, which leads to unfavorable ratios of dinuclear-to-multinuclear fusion products.

SUMMARY OF THE INVENTION

It is often desirable to selectively and controllably alter the biochemical, and genetic properties of single cells. To address this challenge and to overcome the shortcomings of bulk electrofusion, the inventors of the present invention have developed a technique to fuse together a single pair of cells at a time. The ability to controllably fuse together single cells represents a technique by which the long-term genetic identity and behavior of a selected cell can be precisely manipulated, and opens up new possibilities to create combinatorial libraries of hybrid, and cloned cells. In combination with a powerful measurement and imaging technique, the genetic and biochemical nature of single cells can be studied in detail.

Alteration of cellular properties can also be achieved by fusing together a synthetic phospholipid vesicle with the desired vesicular content and membrane compositions to a target cell. This technique can be used to alter the contents and membrane properties of single cells. It is, for example, possible to introduce a membrane protein reconstituted in liposomes into the cell plasma membrane. This ability to selectively transform the membrane composition of single cells is anticipated to have useful biological applications, such as the introduction of surface receptors for the screening of potential ligands and related pharmacological compounds.

Thus, the present invention provides a novel method for the selective electrofusion of cellular structures, such as cells and liposomes. This method offers the advantage of cell-selection, fusion of adherent cell structures with a high spatial resolution, giving the possibility to create complex cellular networks. As electrofusion is a mild method, this miniaturized version can, for example, be used for cloning on the single cell level and for in vitro fertilization. For cloning experiments in particular, the shortcomings of bulk electrofusion is overcome with the present technique as it offers complete control over the fusion process and any doubts to the identity of the somatic cells needs not to be raised. Also, this method, preferentially in combination with micromachined chip technology, can be used to create screening libraries of cloned cells or hybrid cells.

The characterizing features of the invention will be evident from the following description and the appended claims.

BRIEF DESCRIPTION OF THE DRAWINGS

In the description and the examples below, reference is made to the accompanying drawings on which:

As shown in FIG. 2 G, no resulting background fluorescence is detected, and this illustrates that selective delivery of a drug to the surface (electropermeabilization of the liposome), or interior (electrofusion between the cell and liposome) is possible.

FIG. 3 A shows PC12 cells during dielectrophoresis (0.3-3 kV/cm, 2 MHz). FIG. 3 B illustrates initiation of the fusion by the last fusion pulse (6 pulses of 1 ms duration per each, 3 kV/cm), this can be seen by a broader and flatter contact zone between the cells. FIG. 3 C (~1 minute after the fusion pulses) and FIG. 3 D (~2 minutes after the fusion pulses) show the subsequent broadening of the fusion area between the cells, indicating complete fusion.

FIGS. 4 D-E show fusion between a NG-108 cell (protease-treated for 30 minutes) and a PC liposome with incorporated γ-glutamyltransferase (γ-GT). In FIG. 4 E it is seen how the microelectrode is gently pulled away from the cell, and the liposome (which is attached to the microelectrode) is stretched but does not detach from the cell.

DETAILED DESCRIPTION OF THE INVENTION

Figure 1:
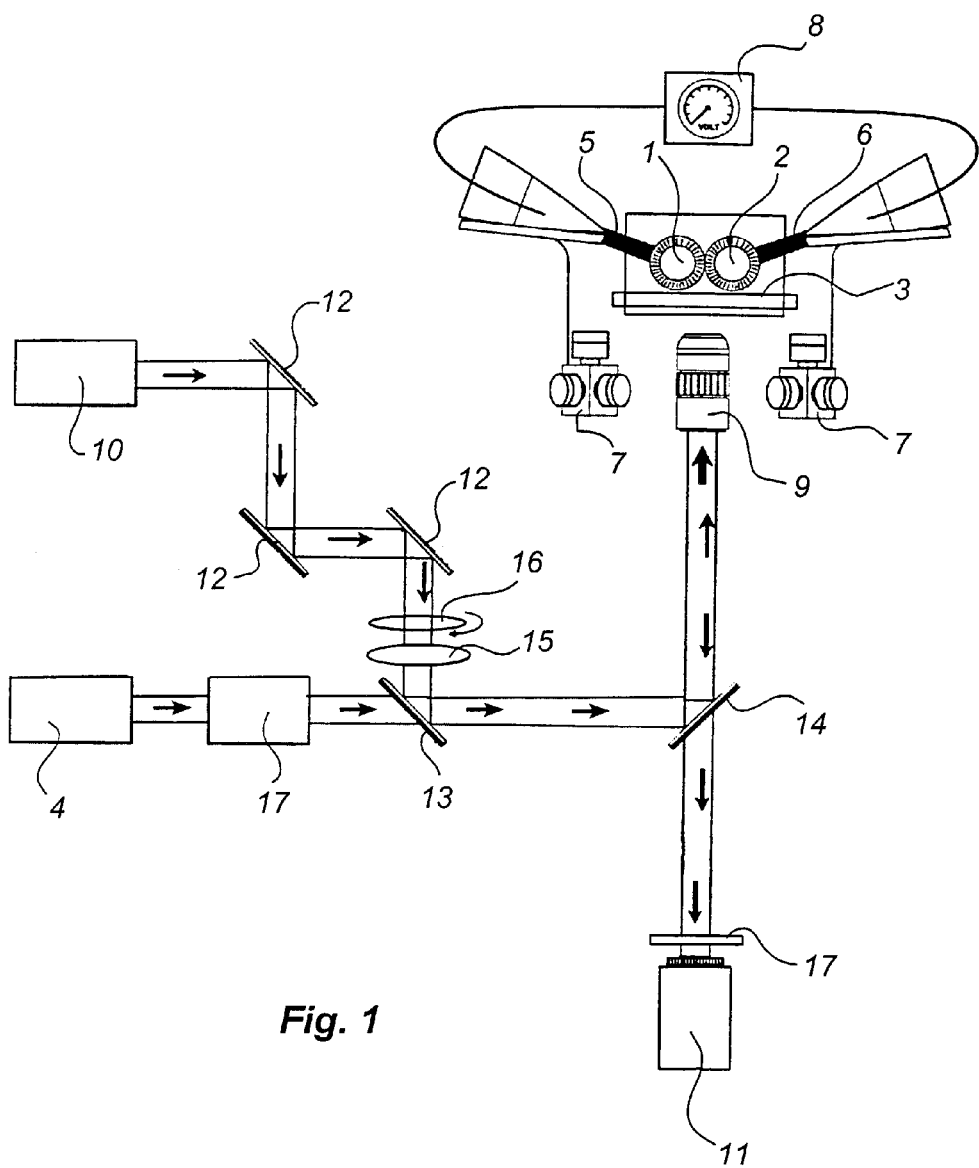
FIG. 1 is a schematic drawing showing the experimental set up. Cells 1, 2 are added from suspension to a microscope coverslip 3 mounted in a polycarbonate holder. The cells are either prealigned using optical trapping (MOPA laser 4) or simply by pushing them together with the microelectrodes 5, 6 controlled by high-graduation micromanipulators 7. For fluorescence imaging and optical trapping, two collinear laser beams are sent into the microscope objective 9; an argon ion laser 10 (black, thin arrows) is used to excite fluorescein, and a MOPA diode laser 4 (black thick arrows) is used for optical trapping. The resulting fluorescence and bright field images are directed to a CCD camera 11.

The invention relates to a method for selective electrofusion of at least two fusion partners having cell-like membranes, comprising the following steps: A) the fusion partners are brought into contact with each other, and B) an electrical field of a strength sufficient to obtain fusion and highly focused on the fusion partners is applied.

Said at least two fusion partners having cell-like membranes are preferably structures of cellular or sub-cellular dimensions. The expression "structure of cellular or subcellular dimensions" relates in particular to biological structures such as independent cells and smaller structures, but it also relates to similar artificial structures. Thus, the fusion partners may be, independently of each other, a single cell, a liposome, a proteoliposome, a synthetic vesicle, a plant protoplast, an egg cell, a sperm or spermatid, and an enucleated egg cell.

As stated above, the fusion partners are brought into contact with each other. This means either that they are placed so that the outer surfaces of the fusion partners are touching, or that the fusion partners are placed at a very small distance from each other.

In most cases the method according to the invention is used for fusion of two fusion partners, below denoted Fusion Partner I and Fusion Partner II, however it, is also possible to fuse more than one fusion partner. In some cases it is especially interesting to fuse more than two partners, for example, to create multinuclear cells with more than two nuclei, or when one of the partners is of much larger dimensions than the others. An example of this is when one wishes to introduce a substance contained in vesicles into a cell. In this case Fusion Partner I is the cell and Fusion Partner II is several of the smaller vesicles.

Furthermore, it is possible to repeat the method according to the invention one or several times, so that a new fusion partner is fused to two already fused fusion partners. This is of particular importance when combinatorial libraries of cloned cells and hybrid cells are created.

When Fusion Partner I is a cell and Fusion Partner II is a single liposome, the fusion of them allows both the introduction of the liposomal content into the cell interior as well as the addition of lipids and membrane proteins from the liposome membrane into the cell surface. This cell-liposome fusion represents a novel approach to the manipulation of the membrane contents and surface properties of single cells.

To fuse Fusion Partner I, such as a cell, a liposome or another similar structure, to Fusion Partner II, such as a cell, liposome or similar structure, it is necessary to place the two fusion partners next to each other, i.e. in contact with each other. The fact that the two fusion partners are placed next to each other before fusion makes it possible to avoid dielectrophoresis, which traditionally is used for the creation of close contact between cells. However, dielectrophoresis can be used successfully in combination with this invention to create and establish close cell-cell contacts before the dc-field fusion pulse is applied. Mechanically, close contact between the fusion partners can be done in any suitable way. Individual manipulation of the two fusion partners for alignment facilitates this alignment. Using, for example, optical trapping with highly focused laser beams, individual cells, as well as other biological structures, including organelles of small dimension, can be manipulated and moved at will [this has been described previously, see e.g. Jaroszeski, M. J., et al., 1994. Mechanically facilitated cell-cell electrofusion, Biophys. J., 67, 1574-1581; Uchida, M., et al., 1995, Whole-cell manipulation by optical trapping, Curr. Biol., 5, 380-382; Chiu, D. T., et al., 1998, Probing single secretory vesicles with capillary electrophoresis, Science, 279: 1190-1193]. When electrodes are used for positioning of the fusion partners, as described below, it is possible to align the two fusion partners by adjusting their positions by moving them with the tips of the electrodes. In order to move the electrodes it may be advantageous to use a microscope, at least one micropositioner and/or a stereotactic device. To further facilitate the positioning of the two fusion partners, it may be advantageous to immobilize one of the fusion partners prior to performing step A. When electrodes are used, this may, for example, be done by reversibly adhere at least one of the fusion partners to at least one of the microelectrodes. In some cases it may be advantageous to use dielectrophoresis, as pretreatment of the two aligned cells, before fusion. This can be done by connecting an ac-field sweep function generator to the electrodes.

The electrical field may be obtained by use of a low-voltage or high-voltage pulse-generator depending on the electrodes used, and other experimental parameters. The voltage generator is used to produce an electric field strength sufficient to result in fusion between the two fusion partners, approximately 0.1-10 kV/cm, for durations of 10 μs to several seconds. The voltage measured at the membrane of the fusion partners should be between a few hundred millivolts to several volts, preferably around 1.5V. In the case of multiple-voltage-pulse protocols, we have found that a pulse repetition rate of approximately 1 Hz, to be suitable, however, other repetition rates might work well. For longer pulse-application durations, correspondingly, repetition rates of a lower frequency should be used. In any event, the length and the strength of the pulses depend on the size of the partners to be fused. Preferably, the fusion pulses have a rectangular waveform, but other waveforms works as well, including various ac-field pulse protocols. For dielectrophoresis, the sweep function generator preferably generates a alternating field, sinus-wave form, of field strengths between 100 V/cm-5 kV/cm, 100 Hz-2 MHz.

The electrical field used in step B to obtain fusion should be highly focused in order to avoid affecting any surrounding structures and to obtain the advantages of the present invention. To focus the electrical field it is preferable to provide the electrical field by use of one or two microelectrodes positioned close to the two fusion partners, i.e. 0-10 μm, preferably 0-5 μm, from the cellular membrane. In the case of using a single electrode, this electrode is preferably, biased at a positive potential (anode) and work against a grounded cell preparation. According to the invention the microelectrodes are preferably electrodes of cellular to subcellular dimensions. Preferably the outer dimension of the ends of the electrodes positioned closest to the fusion partners is from a few nanometers to ~100 micrometers, more preferably 5-30 micrometers and most preferably approximately 20 μm. The electrodes can be made of a solid electrically conducting material, or they can be hollow for delivery of fusion partners or chemical agents of choice. The electrodes can be made from different materials. A special type of electrodes are hollow and made from fused silica capillaries of a type that frequently is used for capillary electrophoresis and gas chromatographic separations. These capillaries are typically one-to-one hundred micrometers in inner diameter, and five-to-four hundred micrometers in outer diameter, with lengths between a few millimeters up to one meter. For cell fusion applications, these electrodes are filled with an electrolyte, preferably a physiological buffer solution. When a potential sufficient to cause cell-fusion is applied over the capillary, electroendoosmotic bulk flow is induced in the capillary, which in combination with Pouiseille flow (gravitational flow in capillaries) can be used to efficiently transfer materials to the fusion partners. Such hollow narrow-bore fused silica capillaries have the additional advantage that components added to the inlet end can be fractionated based on their charge-to-frictional drag ratio. This characteristic feature of the system can be used to, for example, investigate the effect of various fractionated components on cell fusion.

Furthermore, it is preferred to provide the two fusion partners in an electrofusion buffer prior to step B.

In order to facilitate the fusion, it may be advantageous to pre-electroporate at least one of the fusion partners before step A is performed.

When one (or both) of the fusion partners is a cell, it may be part of a cellular network or a tissue, for example, in order to study cellular networks where, for example, the alteration of the biochemical identity of a selected cell can have profound effects on the behavior of the entire network.

A setup suitable for performing the method according to the invention is illustrated in FIG. 1. In this figure the two fusion partners 1, 2 both are cells. The cells to be fused are added from a suspension to a microscope coverslip 3 mounted in a polycarbonate holder.

The cells are either prealigned using optical trapping (MOPA laser 4) or simply by pushing them together with the microelectrodes 5, 6 controlled by high-graduation micromanipulators 7. The microelectrodes are preferably carbon fiber electrodes, and most preferably carbon fiber ultramicroelectrodes (5 μm in diameter), or hollow glass fiber electrodes.

A voltage generator 8 is used to provide the required electrical field.

For fluorescence imaging and optical trapping, two colinear laser beams are sent into the microscope objective 9. A 488-nm beam from an argon ion laser 10 (the beam from the argon ion laser is denoted by black, thin arrows) was used to excite fluorescein and a 992-nm beam from a MOPA diode laser 4 (the beam from the argon ion laser is denoted by black, thick arrows) was used for optical trapping.

The resulting fluorescence and bright field images are directed to a CCD camera 11.

The setup also comprises mirrors 12, a dichroic beamsplitter 13, a polychroic beamsplitter 14, a lens 15, a spinning disc 16, and a filter 17.

The method according to the invention is suitable for manipulating the genetic identity and biochemical surface properties of individual cellular or sub-cellular structures, such as organelles. It is especially suitable and interesting for in vitro-fertilization. It can also be used in several other applications such as cloning, creation of hybridomas, manipulation of the composition of a cellular membrane, and delivery of a well-defined volume of a substance to a cell (particularly delivery of a pharmaceutically active substance to a cell).

The method according to the invention is also suitable for electrofusion in vivo of patients or animals suffering from biochemical disruptions in individual groups of cells.

Many diseases, may they be genetically acquired or not, results in metabolic disruptions. For example, Parkinson's disease caused by degeneration of neurons in the Nigro-striatal pathway result in malfunctioning in the biochemical machinery for production of dopamine in an isolated population of cells. This in turn results in motorbehavioral deficits. The standard treatment of Parkinson's disease is by oral administration of L-DOPA, a precursor of dopamine. Alternatively, grafted tissue with neuronal cells producing dopamine is transplanted into the patient's brain. Intracellular drug or gene-administration in vivo into the appropriate brain structures can be accomplished using an electrofusion procedure similar to that described in the above examples and used as a therapeutic strategy.

Other diseases were a small population of cells are malfunctioning include many disorders in the inner organs, but also tumors.

Experimental treatment of brain tumors using genetically engineered viruses for gene delivery has been used with anecdotal reports of success. However, the use of viruses as a delivery system has limitations in that it might pose a potential hazard should the virus mutate. Using an electrofusion procedure for gene delivery (e.g. "suicide genes" cytokine deaminase or thymidine kinase) similar to that described in the examples below eliminates the need for the use of virus delivery systems in cancer therapy.

Many times a focal administration (administration directly to the malfunctioning set of cells) of drugs or genes (gene therapy) can be expected to be far superior than intraperitoneal, oral, intraventricular, or any other kind of commonly employed drug-administration technique. Intracellular drug-and-gene-administration in vivo can be accomplished using an electrofusion procedure similar to that described in the examples below. Because of the extremely small dimensions of the electrodes, in combination with the low voltages applied, very little tissue trauma is expected. Furthermore, the positioning of the electrodes and the subsequent gene or drug delivery is very precise. This is especially important in the brain. It has been shown that microdialysis probes, which are on the order of a hundred times larger than the electrodes employed here for electroporation, cause very little tissue trauma and disruption of local metabolism 24 hours after implantation.

For solute transfer into cells and organelles in vivo using electroporation it is preferred to use electrodes which are hollow. The fusion partner to be electrofused into cells are then simply administered through the narrow channel in the center of the electrode by application of a flow by means of a syringe pump or a peristaltic pump or any other type of solution pumping system including electrophoresis.

An especially interesting possibility is to use battery-operated perfusion/electroporation implants in bio-tolerable materials for continuous application of solutes with fusion partner for electrofusion into cells or tissue. Because such low potentials are required, batteries with emf's in the range of a few to 20 volts can be used. These battery-operated electroporation units can be made small, virtually they can be included on a chip measuring only a few millimeters squared.

Figure 5:
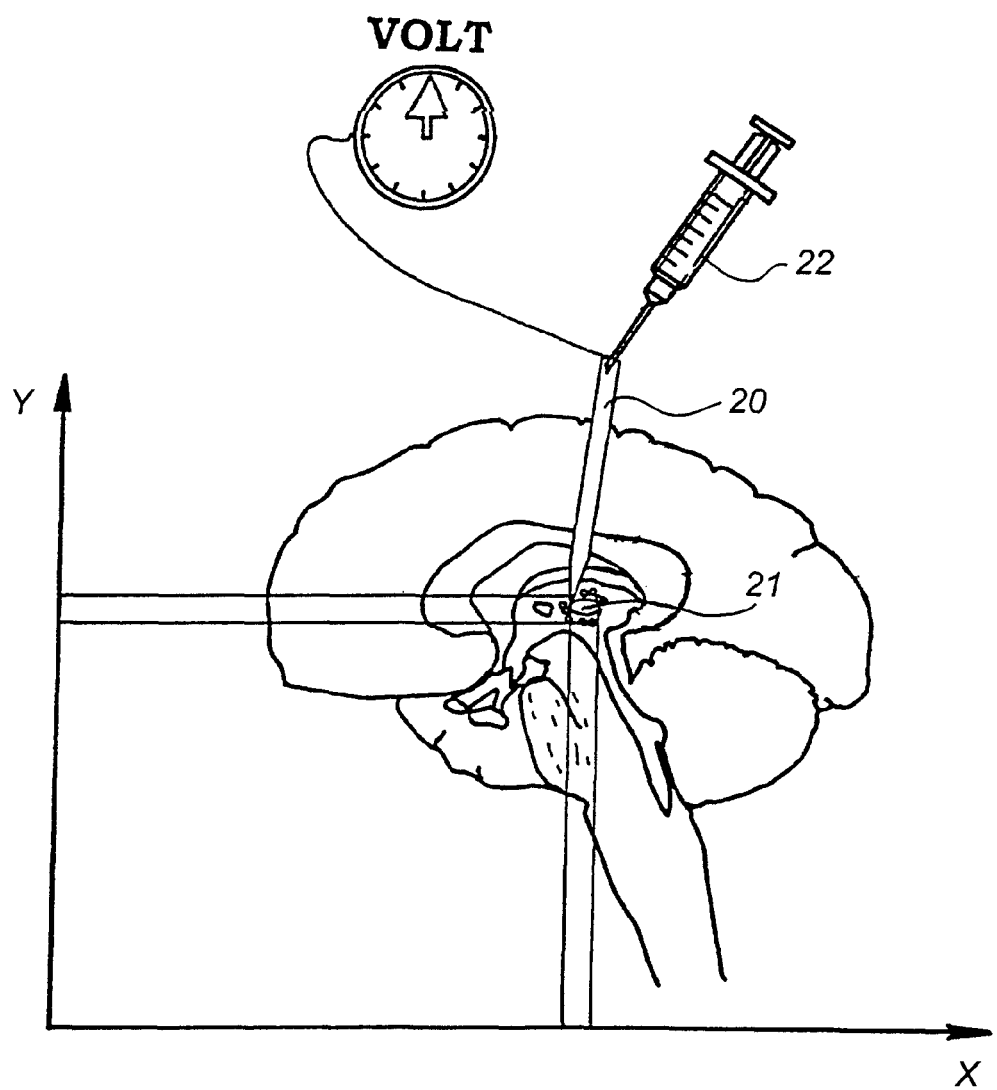
FIG. 5 illustrates an example of a clinical application of the method according to the invention, wherein single or multiple cells in the brain are electrofused to incorporate the content of the other fusion partner. The fusion partner is delivered via a hollow electrode. The electrode is positioned using a stereotactic device, represented in the figure by the Cartesian co-ordinate system, and stereotactic micropositioners.

An example of an in vivo setup is shown in FIG. 5. A hollow electrode 20 is positioned by use of a stereotactic device close to a cell 21 in the brain. This cell 21 constitutes one of the fusion partners. The other fusion partner is constituted by liposomes containing a pharmaceutically active substance, such as DNA, a protein, RNA or a drug. The cell is perfused with the liposomes by injection of the second fusion partner into the electrode 21, either by use of a syringe 22 as shown in the figure, or by use some other appropriate means.

The invention will now be further explained in the following example. This example is only intended to illustrate the invention and should in no way be considered to limit the scope of the invention.

EXAMPLES

In the examples, the following methods and materials were used.

Micromanipulation and Fusion

Figure 2:
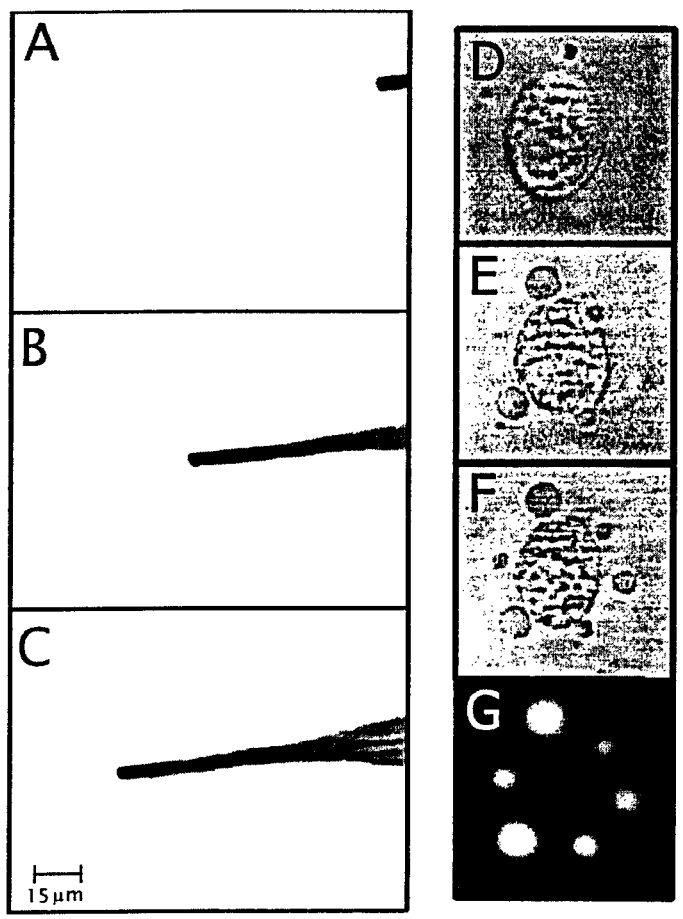
FIGS. 2 A-C show the alignment of a liposome with a selected cell using a microelectrode, and FIGS. 2 D-E show six fluorescein-containing (10 μM) liposomes brought into contact with a cell.

Optical trapping with highly focused laser beams was used to align the fusion partners. Using this procedure, one of the fusion partners (cell or liposome) in solution was trapped by an IR laser beam and brought into contact with the other fusion partner, which was either an adherent cell grown on a substratum or a cell placed on the substratum using, optical trapping with the set-up schematically shown in FIG. 1, and described above. For positioning of cells or liposomes close to cellular targets for fusion, the inventors also use reversible adsorption to carbon fiber microelectrode tips. In using this particular scheme for cell-liposome fusions, liposomes co-immobilized with cells on poly-L-lysine-coated glass surfaces are detached from the surface by pushing the electrode tip against the liposome roughly parallel to the object plane. The liposome will then adhere lightly to the electrode tip and can be relocated close to a cellular structure by micromanipulators that can be moved in increments of 0.2 µm in three dimensions. This is shown in FIGS. 2 A-C, where a liposome of about 5 µm in diameter is moved about 90 µm to a target cell, while FIGS. 2 D-G show how complex cell-liposomal patterns can be created using this simple approach. The liposomes in FIGS. 2 A-C were first immobilized on poly-L-lysine-coated boro-silicate coverslips, and cells were added in suspension. A liposome could easily be moved over 90 µm to a cell. One advantage of this technique over optical trapping is the much larger force that can be applied to the vesicles. The same method can be used for the alignment of two cells, with the exception that poly-L-lysine-coated coverglasses do not have to be used as the cells in suspension simply attach to the surface due to gravity.

For electrofusion, the same pair of 5 µm-outer diameter carbon fiber microelectrodes is used. FIG. 1 depicts the geometrical arrangement of the electrodes with respect to a pair of cells prealigned for fusion. For cell-cell, and cell-liposome fusion, highly focused electrical fields are applied using a low-voltage pulse-generator. An advantage of this set-up is that the electrodes are of cellular to subcellular dimensions, enabling fusion of single cells in complex cellular networks grown on a substratum. At the same time, the highly focused electric field minimizes the risk for unwanted fusion or electroporation of surrounding cells.

Experimental Protocol

Optical Trapping, Microscopy, and Fluorescence Imaging

The optical trapping and fluorescence imaging systems were built in-house. The optical trap was formed by sending the output from a single-mode MOPA laser diode (Model SDL-5762-A6, SDL, Inc.) through a spatial filter (model 900, Newport) so that the output was then reflected off a near-IR mirror. The reflected laser light was passed through a dichroic mirror, reflected from a polychroic mirror (Chroma Technology Corp.) that is placed in a microscope (Nikon Diaphot or Leica DM IRE), and subsequently brought to a diffraction-limited focus with a high-numerical aperture objective (100×, NA 1.4 Nikon and 100×, NA 1.3 Leica, respectively). Fluorescence excitation was achieved by sending the 488-nm output of an argon ion laser (Spectra Physics 2025-05) through a telescope followed by a spinning disc. The purpose of the spinning disc is to scatter the laser light so that uniform illumination is achieved for fluorescence imaging. The scattered laser light from the disk was collected by a lens and reflected from a dichroic mirror (Chroma Technology Corp). This reflected light was sent into the microscope and was reflected by a polychroic mirror. Fluorescence and brightfield imaging was performed by a 3-chip color CCD-camera (Hamamatsu) or a silicon-intensified target camera (Hamamatsu) and recorded by a Super VHS recorder (Panasonic) or dumped directly to a hard disk via a frame grabber.

Electrofusion Instrumentation

For electrofusion experiments, cell dishes were mounted in a circular polycarbonate holder using vacuum grease, and transferred to the stage of an inverted microscope. Two carbon fiber microelectrodes (Axon Instruments, Inc. ProCFE) with an outer diameter of 5 µm were positioned close at each side of the respective fusion partner by high-graduation micromanipulators (Narishige MWH-3). The two carbon fiber electrode tips (anode and cathode) were positioned at an angle of 0-20°, and 160-180° with respect to the object plane. Cells were fused with multiple 1-ms pulses, using a pulse generator (Digitimer Stimulator DS9A) or a homebuilt variant. The voltage output from the pulsegenerator was calibrated using high-impedance electrodes and a patch-clamp amplifier. The electrofusion buffer was either a 0.3 mol/kg Hanks Hepes solution (137 mM NaCl, 5.4 mM KCl, 0.41 mM $MgSO_4$, 0.4 mM $MgCl_2$, 1.26 mM $CaCl_2$, 0.64 mM $KH_2PO_4$, 3.0 mM $NaHCO_3$, 5.5 mM D-glucose, 20 mM Hepes, pH adjusted to 7.4 with NaOH) or a 0.2 mol/kg Hepes Saline buffer (135 mM NaCl, 5 mM KCl, 10 mM glucose, 2 mM $MgCl_2$, 2 mM $CaCl_2$ and 10 mM HEPES) diluted with 30-50% MilliQ-water. For PC12 cells were standard iso-osmolar and hypo-osmolar fusion media used, 300 L3 and 75 L3 receptively [Foung, S. et al, J of Immunol Methods, 134, 35-42].

For the NG-108 and Cos 7 cell-cell fusion experiments, 5% PEG 4000 was added to the fusion media, and in the cell-liposome fusions, 1.25% DMSO was added.

Cell Culture

Jurkat, NG 108, COS 7, and PC12 cells were cultured according to standard procedures. The NG-108 and Cos 7 cells were treated with protease (from *Aspergillus Oryaze*) 2 mg/ml, for 5-30 min in incubator (37 degrees Celsius, 90% humidity and 5% $CO_2$ atmosphere).

Preparation of Fluorescein-Encapsulated Unilamellar Vesicles and Fluorescently Labeled Proteoliposomes Liposomes from L-α-phosphatidylcholine in chloroform (powder from fresh egg yolk, Sigma St. Louis, Mo.) were obtained in high yield using a rotary evaporation method [as described e.g. in Moscho, A., et al., 1996, Rapid preparation of giant unilamellar vesicles, Proc. Natl. Acad. Sci. USA 93: 11443-11445]. Fluorescently labeled γ-GT was prepared by reacting with 2.3 mM fluorescein isothiocyanate (FITC). Unreacted FITC was removed by running the γ-GT-FITC solution through an Econopac 10DG column (BioRad Laboratories, CA), with a 6000 D cut-off. Labeled γ-GT was then incorporated into the vesicle during the vesicle formation process.

Preparation of poly-L-lysine-coated Cover Slips

Cover-slips (borosilicate, 28 mm in diameter, 0.13-0.17 mm thick, Kebo, Sweden) were washed in 70% ethanol/water solution (v/v), followed by MilliQ-water. The glasses were placed in a poly-L-lysine (Sigma-Aldrich Europe)/MQ-water solution (0.1% (w/v)). Cover slips were mounted in a circular polycarbonate holder using vacuum grease. 1 ml of liposome solution was added. After 30 minutes a sufficient number of liposomes were immobilized, and the outside solution could be changed and cells added.

Micromanipulation of Liposomes and Cells Using Microelectrodes

For translation of liposomes to different locations on poly-L-lysine-coated borosilicate surfaces, carbon fiber microelectrodes controlled by high-graduation micromanipulators (Narishige, Japan, 0.2 μm resolution) were used simply by using a combined pushing/scraping movement to loosen the vesicles from the surface. After the vesicles were detached from the surface, they adhered to the electrode tip and could be moved over long distances and be launched close to a cellular target. To determine whether significant loss of the liposomal content is a result of this handling, liposomes were primed with fluorescein (10 μM), attached to the cover slips and washed thoroughly so the fluorescence background was significantly reduced. Comparison between the intravesicular fluorescence intensity before and after moving the vesicles did not show signs of substantial loss of content (data not shown).

Chemicals and Materials

Hepes (>99%), sodium chloride, potassium chloride, and sodium hydroxide (all Suprapur), calcium dichloride, magnesium dichloride, magnesium sulfate, potassium dihydrogen phosphate, PEG 4000 and sodium hydrocarbonate, were purchased from Merck. D-glucose (AnalaR) was from BDH Limited Poole and fluorescein (GC-grade), γ-GT, Protease (type XXIII, from *Aspergillus oryzae*), fluorescein (sodium salt), and DMSO were obtained from Sigma-Aldrich, Sweden. Fluorescein isothiocyanate was from Molecular Probes, Europe. Deionized water from a Milli-Q system (Millipore) was used.

Example 1

Cell-Cell Fusion

Figure 3:
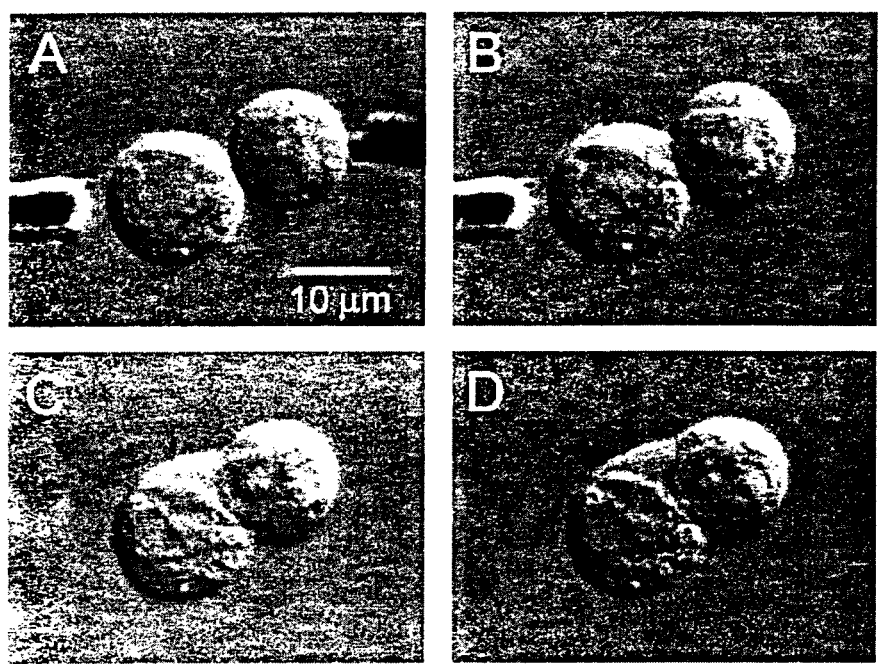
FIGS. 3 A-D show a cell-cell fusion sequence.

In this example two PC 12 cells (≈8 and 10 μm in diameter) brought into contact by optical trapping and immobilized on a cover slip were fused, as shown in FIGS. 3 A-D. FIG. 3 A shows PC12 cells during dielectrophoresis (0.3-3 kV/cm, 2 MHz). FIG. 3 B illustrates initiation of the fusion by the last fusion pulse (6 pulses of 1 ms duration per each, 3 kV/cm), this can be seen by a broader and flatter contact zone between the cells. FIG. 3 C (~1 minute after the fusion pulses) and FIG. 3 D (~2 minutes after the fusion pulses) show the subsequent broadening of the fusion area between the cells, indicating complete fusion.

To demonstrate the high spatial resolution achieved with this technique, individual NG 108 cells in a network were fused (data not shown). In addition to PC 12 cells, and NG 108 cells, Jurkat cells, and Cos 7 cells, were successfully fused (data not shown). Hybrid cells between PC12 cells and NG 108 cells were successfully created in similar fusion protocols (data not shown).

Because of the presence of cytoskeleton, fused cells take much longer to reorganize its membrane and become spherical compared to liposomes. For example, typical liposome-liposome fusion, using an identical experimental set-up, is in the milliseconds regime (data not shown). For some cells with extensive cytoskeletal scaffolding, membrane reorganization can take minutes. However, fusion as characterized by the initial cytoplasmic continuity still occurs within a second. It was generally observed that fusion of cells pre-electroporated in a 0.2 mol/kg buffer were much faster than the fusion of cells held in an isotonic 0.3 mol/kg buffer. The fusion process from initial cytoplasmic continuity to totally fused cells in an isotonic media took several hours. This is consistent with earlier accounts on the fusion media's impact on membrane fusion events, like exocytosis [as described e.g. in Weber, G. et al., 1992, Manipulation of cells, organelles, and genomes by laser microbeam and optical trap, Int. Rev. Cyt., 133: 1-41] and cell-cell fusion [as described e.g. in Zimmerberg, J., et al., 1980, Micromolar $Ca^{2+}$ stimulates fusion of lipid vesicles with planar bilayers containing a calcium-binding protein, Science, 210, 906-908; Scmitt, J. J., et al., 1989, Enhanced hybridoma production by electrofusion in strongly hypo-osmolar solutions, Biochim. Biophys. Acta, 983, 42-50; Scmitt, J. J., et al., 1989, Electrofusion of osmotically treated cells. Naturwissenschaften, 76, 122-123]. Lately it has been argued that the electrofusion enhancement reached by hypo-osmotic fusion media is due to spectrin denaturation [as described e.g. in Zimmermann, U., et al., 1990, Efficient hybridization of mouse-human cell lines by means of hypo-osmolar electrofusion, Journal of Immunological Methods, 134, 43-50; Chemomordik, L. V., et al., 1991, Evidence that the spectrin network and a nonosmotic force control the fusion product morphology in electrofused erythrocyte ghosts, Biophys. J., 60, 1026-1037].

In all NG-108 and Cos 7 fusion experiments, the cells were treated with protease (5-30 min), and for the NG-108 cells the cell fusion media contained 5% (w/v) PEG 4000 [as described e.g. in Sowers, A. E., 1995, Membrane skeleton restraint of surface shape change during fusion of erythrocyte membranes: evidence from use of osmotic and dielectrophoretic microforces as probes, Biophys. J., 69, 2507-2516]. The requirement of different pretreatment and fusion conditions for the respective cell-lines are in agreement with previous observations for cell fusion.

It is well-established that electrically fused cells are biologically intact and continue to grow. Also in our fusion protocol, cells adhered to surfaces and continued to grow when inspected five-to-twentyfour hours post-fusion.

Example 2

Cell-Liposome Fusion

Previous accounts of cell fusion have demonstrated that in addition to mammalian cells of other phenotypes, synthetic vesicles, as well as plant protoplasts can be fused to mammalian cells. Synthetic vesicles have been fused with cells using some kind of chemical treatment or such, for example PEG [as described, for example, in Stoicheva, N. G., et al., 1994, Electrically Induced fusion of mammalian cells in the presence of polyethylene glycol, J. Membr. Biol., 140: 177-182] or by using HVJ-glycoprotein-reconstituted liposomes [as described in Seibicke, S., et al., 1988, Fusion of lipid vesicles with ascites tumor cells and their lipid-depleted variants, Studies with radioactive- and fluorescent-labeled vesicles, Biochim. Biophys Acta, 944, 487-496]. Synthetic lipid-films have been incorporated in the plasma membrane in cells, and micro-injection facilitated, by gentle contact between a lipid-coated glass micropipette and the cellular membrane [as described e.g. in Laffafian, I., et al., 1998, Lipid-assisted microinjection: introducing material into the cytostol and membranes of small cells, Biophys. J., 75, 2558-2563]. Fusion schemes involving synthetic vesicles can be used for purposes of transferring cell-impermeant molecules into a target cell through mixing of contents and for transfer of membrane lipids and membrane associated structures, such as proteins, into the target cell membrane.

Figure 4:
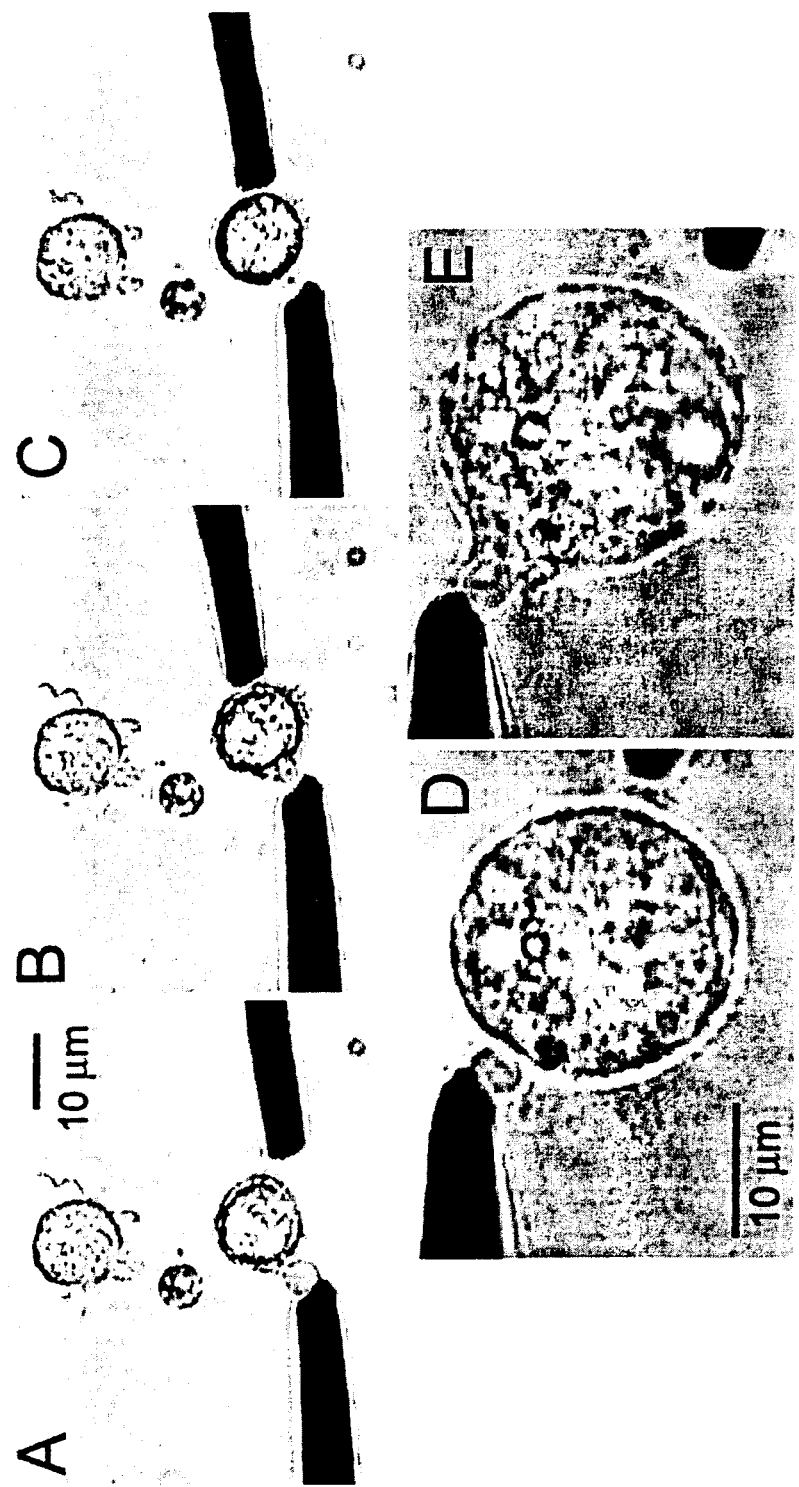
FIGS. 4 A-C show Bright-field images taken before (FIG. 4 A), during (FIG. 4 B), and after (FIG. 4 C) electrofusion (8 kV/cm, 4 ms) of a phosphatidylcholine (PC) liposome (left) with a COS 7 cell (right).

FIGS. 4 A-E are two sequences of images that demonstrate single vesicle-cell fusion according to the invention. In the first sequence (FIGS. 4 A-C) a ≈5 μm diameter phosphatidylcholine vesicle is fused with a ≈12 μm diameter Cos-7 cell, and in the second sequence (FIGS. 4 D-E) a ≈3 μm diameter phosphatidylcholine vesicle with reconstituted γ-GT is fused with a ≈20 μm diameter NG-108 cell (protease-treated for 30 min). This demonstrates the ability of introducing liposome-incorporated proteins into a cellular structure. It is noted that fusion of vesicles with cells was much more difficult to accomplish than fusion between two cells of the same type. Both addition of DMSO (≈2%) to 0.3 mol/kg fusion medium and use of 0.2 mol/kg fusion media were found to facilitate fusion. DMSO has been shown to facilitate both the uptake of DNA using electroporation and increases the yield of fusion, and the use of hypo-osmolar medium is well-known to increase the fusion yield of cells (see above). In the experiment shown in the figure, the fusions were performed in a HEPES-buffered saline solution, and 1.25% dimethylsulfoxide and 20% MQ-water was added to the external buffer solution to assist vesicle-cell electrofusion.

Example 3

Cell Fusion Using Single Open-Bore Fused Silica Capillaries

Fusion experiments were performed with NG 108 cells, cultivated according to standard procedures and plated onto no. 1 circular cover slips, mounted in a circular polycarbonate holder and transferred to an inverted microscope stage. During all experiments the cell-bath was grounded by a platinum wire. Cells were aligned for fusion using optical trapping. A high voltage power supply (Bertand, Hicksville, N.Y., USA) operated at positive potentials of 1-30 kV was used together with electrolyte-filled fused silica capillaries (30 cm long, 30 mm i.d., 375 mm o.d.) employed as electrodes. The experimental setup was otherwise identical to that depicted in FIG. 1. The fused silica electrodes were sharpened to an approximate outer diameter of 50 mm by grinding the tip with a rotating sandpaper dish. The capillary and buffer container (that connects the inlet end of the capillary to the high-power voltage supply by a platinum wire) was filled with Hanks buffered saline. The sharpened capillary tip (outlet end) was positioned using high-graduation micromanipulators close to one of the fusion partners, typically, less than 10 μm. Fusion of two aligned NG108-15 cells was performed by applying pulses of 5-to-15 kV for 0.1-5 seconds.

It was demonstrated that this method according to the invention is highly efficient for fusion of two cells in a complex system. This is especially important for application in in vivo fusion of cells and other fusion partners.

The invention claimed is:
1. An in vitro method for selective electrofusion of a mammalian cell and a fusion partner each having a cell-like membrane, comprising:
    A) selecting the mammalian cell and the fusion partner;
    B) bringing into contact the mammalian cell and the fusion partner;
    C) providing an electric field using at least one microelectrode, which electric field is of a strength sufficient to obtain fusion of the mammalian cell and the fusion partner, and wherein the electric field is between 0.1-10 kV/cm where the mammalian cell and the fusion partner contact, and said at least one microelectrode is positioned 0-100 μm from the mammalian cell and the fusion partner, wherein said at least one microelectrode is positioned by use of a microscope, at least one micropositioner and/or a stereotactic device, and wherein said at least one microelectrode is sufficiently small to permit the selective fusion of only the mammalian cell and the fusion partner.
2. A method according to claim 1, wherein only one microelectrode, which is sufficiently small to permit the selective fusion of the mammalian cell and fusion partner, is used to provide the electrical field in step C.
3. A method according to claim 1, wherein two or more microelectrodes, each of which is sufficiently small to permit the selective fusion of the mammalian cell and fusion partner, are used to provide the electrical field in step C.
4. A method according to claim 1, wherein one microelectrode, which is movably mounted on a microchip, is used to provide the electrical field in step C.
5. A method according to claim 1, wherein several electrodes, at least one of which is movably mounted on a microchip, are used to provide the electrical field in step C.
6. A method according to claim 5, wherein one or more electrodes are movably mounted on a microchip for combinatorial synthesis of fusion products.
7. A method according to claim 2, wherein said at least one microelectrode, which is hollow, electrolyte-filled, and sufficiently small to permit the selective fusion of the mammalian cell and fusion partner, is used to provide the electrical field in step C, and said microelectrode is also used to deliver fusion partners or chemical agents by electroendoosmosis, electrophoresis, or by Poiseuille flow.
8. A method according to claim 2, wherein the outer diameter of said at least one microelectrode is sufficiently small to permit the selective fusion of the mammalian cell and fusion partner without affecting nearby structures.

9. A method according to claim 8, wherein the outer diameter of said at least one microelectrode is 1-100 µm.

10. A method according to claim 2, wherein at least one microelectrode is used, for delivery of the mammalian cell or fusion partner to the fusion site.

11. A method according to claim 2, wherein step A is performed by use of electrodes.

12. A method according to claim 1, wherein step A is performed by use of optical trapping.

13. A method according to claim 1, wherein step A is performed by use of micropipettes.

14. A method according to claim 1, wherein the fusion partner is selected from the group consisting of a single cell, a liposome, a proteoliposome, a synthetic vesicle, an egg cell, and an enucleated egg cell.

15. A method according to claim 1, wherein the mammalian cell or the fusion partner is provided in a buffer prior to step B.

16. A method according to claim 1, wherein at least one of the mammalian cell or the fusion partner has been immobilized prior to step A.

17. A method according to claim 1, wherein one of the mammalian cell or fusion partner is part of a cellular network.

18. A method according to claim 1, wherein at least one of the mammalian cell or fusion partner has been electroporated in a buffer prior to step A.

19. A method according to claim 1, wherein at least one of the mammalian cell or fusion partner has been exposed to a dielectrophoretic field in a buffer prior to step A.

20. A method according to claim 1, wherein at least one of the mammalian cell or fusion partner has been treated by an agent that promotes close cell-cell contacts.

21. A method according to claim 2, wherein said at least one microelectrode, which is movably mounted on a microchip, is used to provide the electrical field in step C.

22. A method according to claim 3, wherein two or more microelectrodes, at least one of which is movably mounted on a microchip, are used to provide the electrical field in step C.

23. A method according to claim 5, wherein at least one of said microelectrodes is movably mounted on a microchip for combinatorial synthesis of fusion products.

24. The method of claim 1, wherein said mammalian cell is a tumor cell.

25. The method of claim 1, wherein said mammalian cell and said fusion partner are not a sperm cell.

* * * * *